United States Patent
Sitzmann

(10) Patent No.: US 6,476,280 B1
(45) Date of Patent: Nov. 5, 2002

(54) METHOD FOR MAKING NONANITROTERPHENYL

(75) Inventor: Michael E. Sitzmann, Adelphi, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/042,627

(22) Filed: Jan. 11, 2002

(51) Int. Cl.$^7$ .............................................. C07C 205/00
(52) U.S. Cl. ........................................ 568/931; 568/927
(58) Field of Search ................................. 568/927, 928, 568/931

(56) References Cited

U.S. PATENT DOCUMENTS 3,755,471 A   8/1973   Dacons ..................... 260/645

OTHER PUBLICATIONS

Heat Resistant Explosives XIX. An Improved Synthesis of 2,2',2",4,4'4,",6,6',6"–Nonanitroterphenyl, NONA (C), May 3, 1965, J.C. Dacons, J.C. Hoffsommer, and Francis Taylor, Jr.

Primary Examiner—Jafar Parsa
(74) Attorney, Agent, or Firm—Mark Homer

(57) ABSTRACT

The present invention is a method for synthesizing polynitropolyphenyls, and more particularly 2,2',2",4,4',4", 6,6',6"-nonanitroterphenyl (NONA), that employs only a dihalotrinitrobenzene as a starting material. The general method comprises reacting copper dust with dihalo-trinitrobenzene to form a dihalo-polynitropolyphenyl product. This product is then reduced through a high-yield conversion by heating it within a solvent with a reagent capable of providing a source of iodide and a proton source.

19 Claims, No Drawings

METHOD FOR MAKING NONANITROTERPHENYL

STATEMENT OF GOVERNMENT INTEREST

The invention described herein may be manufactured and used by or for the Government of the United States of America for governmental purposes without payment of any royalties thereon or therefor.

BACKGROUND OF THE INVENTION

1. Field of the Invention

The present invention pertains to the field of synthesis of high explosive aromatic nitro compounds, particularly to synthesis of polynitropolyphenyls having heat resistant properties, and, more particularly to synthesis of 2,2',2",4,4',4",6,6',6"-nonanitroterphenyl (NONA).

2. Brief Description of the Prior Art

Because NONA possesses a unique combination of very high thermal stability and high initiation sensitivity, it is a very desirable explosive for many military and commercial applications. Among the numerous military applications, NONA is particularly well suited for exploding foil initiators (EFIs). Compared to HNS (2,2',4,4',6,6'-hexanitrostilbene), which is commonly used for EFIs, NONA has higher temperature stability, higher energy, and a lower threshold for initiation. Regarding commercial applications, NONA is very well suited for use as an initiating explosive in the high temperature environments encountered in deep oil and gas well operations. Some of these uses are described in U.S. Pat. Nos. 6,295,912; 5,149,911; 4,998,477; 4,920,883; 4,777,878; and 4,735,145.

However, despite its attractive properties, NONA is not widely used because it suffers a large disadvantage due to its difficult synthesis and the resulting high cost. The current synthesis method for producing NONA is found in U.S. Pat. No. 3,755,471. This method involves mixed Ullmann reactions between a picryl halide and a dihalotrinitrobenzene, where the halogen group is Cl, Br, or I. The picryl group is 2,4,6-trinitrophenyl. The reaction related to this method is set forth as Reaction I below:

REACTION I

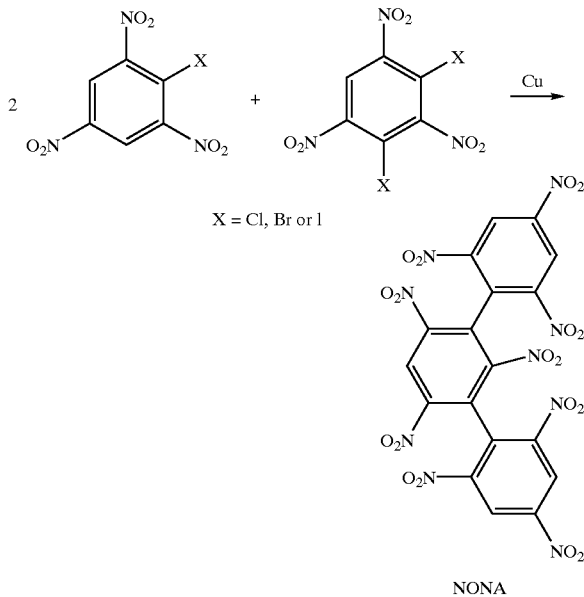

NONA

This method for synthesizing NONA is problematic because the yields are quite low (approximately 20–25%, at the optimum) and the method requires one to separate the NONA from the very large amount of 2,2',4,4',6,6'-hexanitrobiphenyl (HNB) that is produced as the main product. The ease of formation of HNB relative to NONA is due to steric interactions between nitro groups on adjoining trinitrobenzene rings. The formation of NONA requires attaching two picryl groups onto a trinitrobenzene ring. The formation of HNB requires attaching only one picryl group onto a trinitrobenzene ring (shown in the Reaction II set forth below).

REACTION II

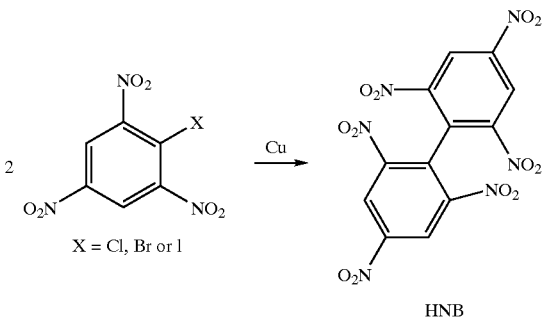

X = Cl, Br or I

HNB

The problems associated with the current method for producing NONA discussed above are reflected in its high cost, and, thus, its current use is limited. Therefore, a method of synthesizing NONA is desired that produces a higher yield and is less costly.

SUMMARY OF THE INVENTION

Accordingly, it is an object of this invention to provide a new method to synthesize polynitropolyphenyls.

It is a further object of this invention to provide a method to synthesize NONA.

It is still a further object of this invention to provide a method to synthesize NONA that costs less than the current method.

This invention accomplishes these objectives and other needs related to synthesis of polynitropolyphenyls by providing a method for synthesis that employs only a dihalotrinitrobenzene as a polynitropolyphenyl starting material. This method thereby avoids the disadvantages inherent in using a mixed Ullmann type reaction as described above. The present invention provides significantly increased polynitropolyphenyl yields compared to the current synthesis method by employing reaction conditions that produce dihalo-polynitropolyphenyls as the predominant product of the intermediate reaction. This intermediate product is then converted into polynitropolyphenyls through high-yield conversion of the dihalo-polynitropolyphenyls product using an iodide source and a proton source in order to replace the halogens on the polynitro rings with hydrogens.

DESCRIPTION OF THE PREFERRED EMBODIMENT

The present invention is a method for synthesizing polynitropolyphenyls that employs only a dihalo-trinitrobenzene as a starting material. The general method comprises reacting copper dust with dihalo-trinitrobenzene to form a dihalo-polynitropolyphenyl product. This product is then reduced through a high-yield conversion by heating it within a solvent with a reagent capable of providing a source of iodide and a proton source.

Reactions III and IV below are examples that further describe this general method using a dihalo-trinitrobenzene to form dihalo-NONA (Reaction III) and the dihalo-NONA is reduced to NONA using sodium iodide as the reagent and acetic acid as the proton source (Reaction IV).

REACTION III

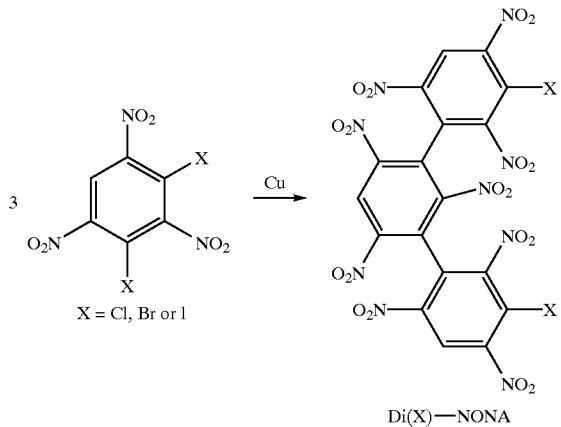

REACTION IV

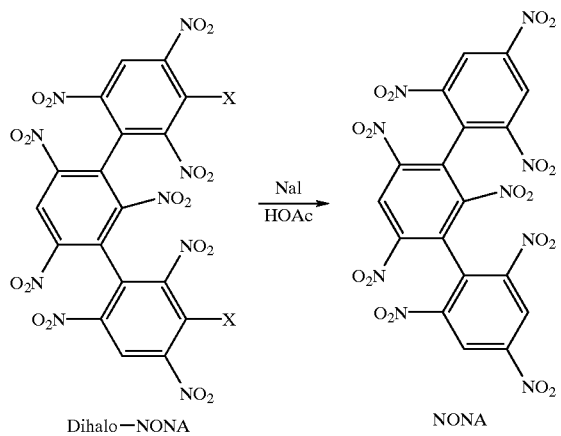

Regarding the first step of the method, a dihalo-trinitrobenzene, preferably dichloro-trinitrobenzene, will normally be mixed with an inert solvent. This inert solvent may be selected by one skilled in the art, but examples include toluenes, xylenes, benzenes, or mixtures thereof. The mixture will then normally be heated, while being vigorously stirred, prior to adding the copper dust. Preferably, the mixture will be heated between 110° C. and 210° C. The copper dust is then added to the mixture in intervals. After the reaction between the copper and the mixture is complete, the resultant is cooled and filtered and the organic products are separated from the inorganic residue. The solvent may be removed from the product by using steam distillation or other methods known by those skilled in the art. The final product from the first step will be dihalo-polynitropolyphenyls. If dichloro-trinitrobenzene is used as a reactant, this will result in dichloro-polynitropolyphenyls. This final product will normally be a combination of different dihalo-polynitropolyphenyls including dihalo-NONA and dihalo-2,2',2",2"',4,4',4",4"',6,6',6",6"'-dodecanitroquaterphenyl (DODECA).

At this point in the process, one may select a particular dihalo-polynitropolyphenyl from the first step product in order to obtain a specific final product from the overall method. For instance, one may obtain an intermediate of pure dihalo-NONA by using fractional crystallization to separate the dihalo-NONA from the other dihalo-polynitropolyphenyls within the final product from the first step above. By using an intermediate product of pure dihalo-NONA obtained in such a manner, one may obtain a final product of NONA as described below.

The final general step in the process comprises reducing the final product from the first step or intermediate product produced by the steps above through a high-yield conversion by heating it within a solvent with a reagent capable of providing a source of iodide and a proton source. The solvent may be any solvent compatible with the reaction and may be selected by one skilled in the art. Specific examples of such solvents include methyl ethyl ketone or acetone. The reagent will provide a source of iodide that may assist in removing the halogens from the polynitro rings of the dihalo-polynitropolyphenyls after forming HI. Some preferred iodide sources include iodine-based salts such as sodium iodide and potassium iodide. The proton source provides the hydrogen atoms that replace the halogen groups on the polynitro rings to produce the final polynitropolyphenyl product. The proton source should be compatible with dihalo-polynitropolyphenyls and may be selected by one skilled in the art. Preferred examples of a proton source include organic acids such as acetic acid and formic acid.

The present invention also includes a polynitropolyphenyl product formed from the process of reacting copper dust with dihalo-trinitrobenzene to form a product comprising a dihalo-polynitropolyphenyl. This dihalo-polynitropolyphenyl product is then reduced by heating in a solvent with a reagent selected from sodium iodide or potassium iodide and an organic acid to form a final product of polynitropolyphenyl.

The general nature of the invention having been set forth, the following theoretical examples are presented as specific illustrations of how one would practice the invention. It will be understood that the invention is not limited to these specific examples, but can be practiced with various modifications that will be recognized by one of ordinary skill in the art.

EXAMPLE 1

Example 1

Preparation of NONA from 1,3-Dichloro-2,4,6-trinitrobenzene (via Purified Dichloro-NONA Intermediate)

A solution containing (1.0 mole) (281 g) of 1,3-dichloro-2,4,6-trinitrobenzene in an inert solvent (approximately 800–1000 ml) is vigorously stirred at 110–210° C. in a 2 liter three neck round bottom flask equipped with a mechanical stirrer, condenser and thermometer (the solvent is chosen from toluene, xylenes, nitrobenzene, etc. or mixtures thereof). Copper dust (0.7 mole) (44 g) is added in approximately 5 g portions at 3 minute intervals, however, there is a 5–10 minute wait after the initial 5 g portion is added to ensure that reaction has begun. (A darkening of the mixture and the loss of the copper sheen is an indication that reaction has begun). After the copper addition is complete, the mixture is held at elevated temperature for 10–15 minutes before it is cooled to 50–60° C. and filtered. The filter cake is washed well with hot acetone until the organic products are removed from the inorganic residue. The solvent is removed from the filtrate by steam distillation and the residue is digested in hot methanol. The methanol-insoluble crude product is dissolved in the minimum amount of hot acetone, the solution is treated with activated charcoal, then filtered, and the filtrate is concentrated by distillation until precipitation begins to occur. Fractional crystallization gives purified dichloro-NONA. The purified dichloro-NONA intermediate is converted to NONA by heating in methyl ethyl ketone with sodium iodide/acetic acid at reflux temperature for several hours (approximately 1 liter methyl ethyl ketone, 150 g sodium iodide, and 300 ml acetic acid per 100 g of dichloro-NONA). The mixture is concentrated and the NONA product is removed by filtration, washed well with water and recrystallized from acetone.

Example 2

Preparation of NONA and/or NONA-DODECA Mixtures from 1,3-Dichloro-2,4,6-trinitrobenzene The above synthesis is employed to produce the reaction product obtained after steam distillation and digestion in hot methanol. This methanol-insoluble crude product (mixture of dichloro-NONA and dichloro-DODECA) is converted to a NONA-DODECA mixture via heating in methyl ethyl ketone with sodium iodide/acetic acid. The NONA-DODECA mixture is a useful product, but, if desired, fractional crystallization can be used to separate the NONA.

What is described are specific examples of many possible variations on the same invention and are not intended in a limiting sense. The claimed invention can be practiced using other variations not specifically described above.

What is claimed is:

1. A method for the preparation of polynitropolyphenyls, comprising the steps of:
    reacting copper dust with dihalo-trinitrobenzene to form a product comprising a dihalo-polynitropolyphenyl; and,
    reducing the dihalo-polynitropolyphenyl by heating in a solvent with a reagent providing a source of iodide and a proton source.

2. The method of claim 1, wherein the proton source comprises an organic acid.

3. The method of claim 2, wherein the reagent comprises an iodine-based salt.

4. The method of claim 3, wherein the organic acid is selected from formic acid or acetic acid.

5. The method of claim 4, wherein the iodine-based salt is selected from sodium iodide or potassium iodide.

6. The method of claim 5, wherein the dihalo-trinitrobenzene comprises dichloro-trinitrobenzene.

7. The method of claim 6, wherein the solvent is selected from the group of methyl ethyl ketone or acetone.

8. The method of claim 7, further comprising the step of mixing the dichlorotrinitrobenzene with a second solvent prior to reacting with copper.

9. The method of claim 8, wherein the second solvent may be selected from the group including toluenes, xylenes, benzenes, or mixtures thereof.

10. The method of claim 9, further comprising the step of filtering the product prior to the reducing step to separate organic products from non-organic residue.

11. The method of claim 10, further comprising the step of removing the solvent from the product prior to the reducing step using steam distillation.

12. A method for the preparation of 2,2',2",4,4',4",6,6',6"-nonanitroterphenyl, comprising the steps of:
    reacting copper dust with dihalo-trinitrobenzene to form a product comprising a dihalo-polynitropolyphenyl;
    separating the dihalo-nonanitroterphenyl from the dihalo-polynitropolyphenyl using fractional crystallization; and,
    reducing the dihalo-nonanitroterphenyl by heating in a solvent with a reagent providing a source of iodide and a proton source.

13. The method of claim 12, wherein the proton source comprises an organic acid.

14. The method of claim 13, wherein the reagent comprises an iodine-based salt.

15. The method of claim 14, wherein the organic acid is selected from formic acid or acetic acid.

16. The method of claim 15, wherein the iodine-based salt is selected from sodium iodide or potassium iodide.

17. The method of claim 16, wherein the dihalo-trinitrobenzene comprises dichloro-trinitrobenzene.

18. The method of claim 17, wherein the solvent is selected from the group of methyl ethyl ketone or acetone.

19. The method of claim 18, further comprising the step of mixing the dichloro-trinitrobenzene with a second solvent prior to reacting with copper.

\* \* \* \* \*